United States Patent
Liprie

(10) Patent No.: US 6,442,822 B1
(45) Date of Patent: Sep. 3, 2002

(54) FLEXIBLE SOURCE WIRE FOR LOCALIZED INTERNAL IRRADIATION OF TISSUE

(75) Inventor: Sam F. Liprie, Calcasieu Parish, LA (US)

(73) Assignee: Interventional Therapies, LLC, Westport, CT (US)

( * ) Notice: Subject to any disclaimer, the term of this patent is extended or adjusted under 35 U.S.C. 154(b) by 0 days.

(21) Appl. No.: 09/169,891

(22) Filed: Oct. 12, 1998

Related U.S. Application Data

(62) Division of application No. 08/556,250, filed on Nov. 9, 1995, now Pat. No. 5,833,593.

(51) Int. Cl.⁷ .................................................. B23P 19/04
(52) U.S. Cl. .......................................... 29/460; 29/428
(58) Field of Search ...................... 29/428, 458, 460, 29/527.1, 527.2, 557, 559, 418, 422, 723; 600/1, 2, 3, 4, 5, 6, 7, 8

(56) References Cited

U.S. PATENT DOCUMENTS 2,865,376 A * 12/1958 Pellier et al. ............... 606/226
3,351,049 A * 11/1967 Lawrence ....................... 600/8

(List continued on next page.)

FOREIGN PATENT DOCUMENTS

| DE | 9102312 | * 6/1992 | .......... A61N/36/04 |
|---|---|---|---|
| WO | WO 93/04735 | * 3/1993 | ............ A61N/5/00 |
| WO | WO 94/25106 | * 11/1994 | ............ A61N/5/00 |
| WO | WO 96/14898 | * 5/1996 | ............ A61N/5/00 |

Primary Examiner—S. Thomas Hughes
Assistant Examiner—Essama Omgba
(74) Attorney, Agent, or Firm—Cantor Colburn LLP

(57) ABSTRACT

A flexible source wire is provided containing a radioactive source that is capable of maneuvering through a tortuous narrow passage to a treatment site within the body. This source wire includes an elongated flexible housing tube with its proximal end (i.e., the treatment end) modified to receive a radioactive core. The preferred embodiment of the source wire is constructed from a material exhibiting little or no memory retention when bent such as certain nickel/titanium alloys. Both ends of the source wire are sealed and the proximal end of the source wire is rounded to allow ease of movement as it travels through the bends and turns in the body.

18 Claims, 4 Drawing Sheets

U.S. PATENT DOCUMENTS

| | | | | |
|---|---|---|---|---|
| 4,323,055 A | * | 4/1982 | Kubiatowicz | 424/1.11 |
| 4,762,130 A | * | 8/1988 | Fogarty et al. | 606/159 |
| 4,763,642 A | * | 8/1988 | Horowitz | 600/7 |
| 4,819,618 A | * | 4/1989 | Liprie | 600/7 |
| 4,834,724 A | * | 5/1989 | Geiss et al. | 604/280 |
| 4,861,520 A | * | 8/1989 | Hooft et al. | 252/644 |
| 4,891,165 A | * | 1/1990 | Suthanthiran | 600/8 |
| 5,084,002 A | * | 1/1992 | Liprie | 600/7 |
| 5,106,360 A | * | 4/1992 | Ishiwara et al. | 600/2 |
| 5,141,487 A | * | 8/1992 | Liprie | 600/7 |
| 5,199,939 A | * | 4/1993 | Dake et al. | 600/3 |
| 5,213,561 A | * | 5/1993 | Weinstein et al. | 600/7 |
| 5,226,888 A | * | 7/1993 | Arney | 604/96 |
| 5,282,781 A | * | 2/1994 | Liprie | 600/3 |
| 5,295,959 A | * | 3/1994 | Gurbel et al. | 604/96 |
| 5,302,168 A | * | 4/1994 | Hess | 600/3 |
| 5,308,356 A | * | 5/1994 | Blackshear, Jr. et al. | 606/194 |
| 5,342,158 A | * | 8/1994 | Isaacson | 414/146 |
| 5,342,283 A | * | 8/1994 | Good | 600/8 |
| 5,354,257 A | * | 10/1994 | Roubin et al. | 600/7 |
| 5,383,856 A | * | 1/1995 | Bersin | 604/101 |
| 5,484,411 A | * | 1/1996 | Inderbitzen et al. | 604/96 |
| 5,503,613 A | * | 4/1996 | Weinberger | 600/3 |
| 5,503,614 A | * | 4/1996 | Liprie | 600/7 |
| 5,540,659 A | * | 7/1996 | Teirstein | 604/104 |
| 5,554,119 A | * | 9/1996 | Harrison et al. | 604/96 |
| 5,575,749 A | * | 11/1996 | Liprie | 600/3 |
| 5,618,266 A | * | 4/1997 | Liprie | 604/21 |
| 5,624,372 A | * | 4/1997 | Liprie | 600/3 |
| 5,643,171 A | * | 7/1997 | Bradshaw et al. | 600/1 |
| 5,782,741 A | * | 7/1998 | Bradshaw et al. | 600/3 |
| 5,833,593 A | * | 11/1998 | Liprie | 600/3 |
| 5,851,171 A | * | 12/1998 | Gasson | 600/3 |
| 5,857,956 A | * | 1/1999 | Liprie | 600/7 |
| 5,957,829 A | * | 9/1999 | Thornton | 600/3 |
| 6,019,718 A | * | 2/2000 | Hektner | 600/3 |
| 6,066,083 A | * | 5/2000 | Slater et al. | 600/8 |
| 6,080,099 A | * | 6/2000 | Slater et al. | 600/8 |
| 6,163,947 A | * | 12/2000 | Coniglione | 29/458 |
| 6,179,768 B1 | * | 1/2001 | Loffler et al. | 600/7 |
| 6,273,850 B1 | * | 8/2001 | Gambale et al. | 600/3 |
| 6,283,910 B1 | | 9/2001 | Bradshaw et al. | |

* cited by examiner

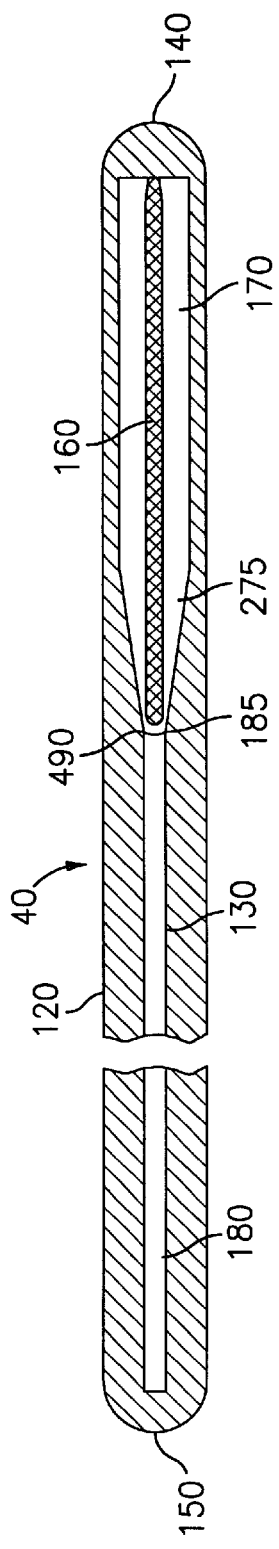
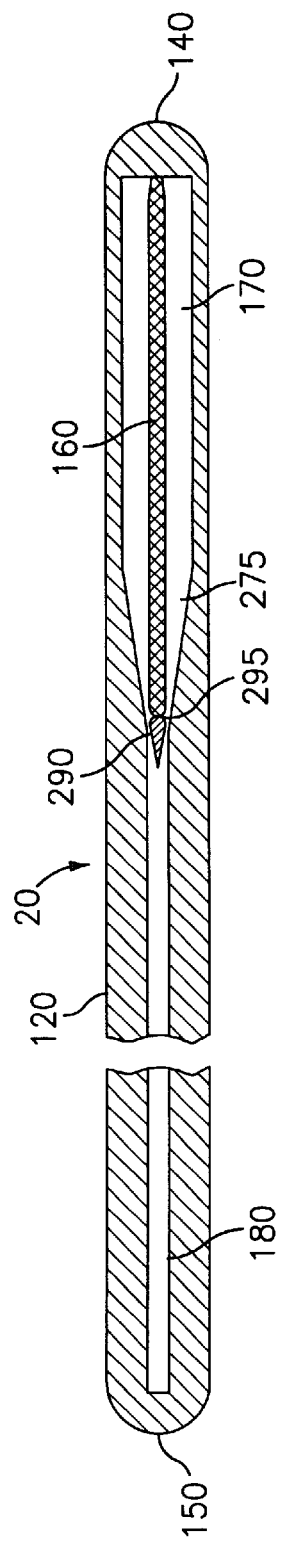
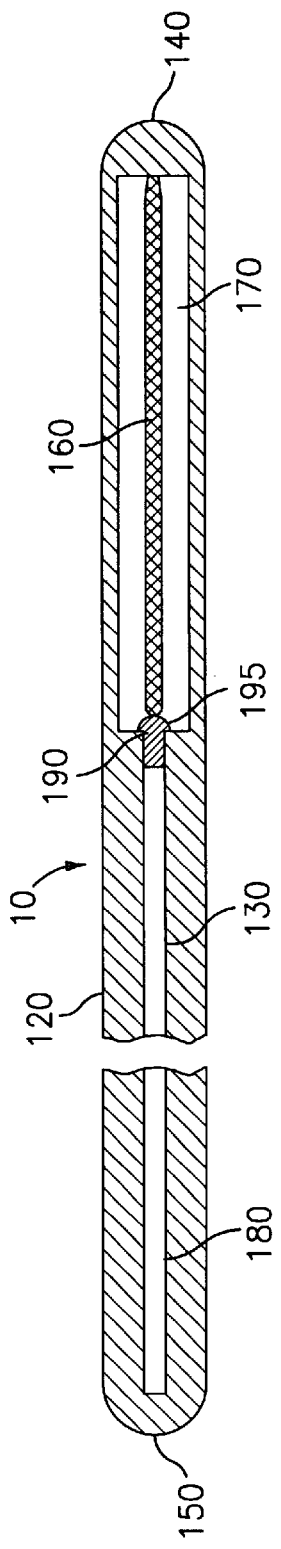

FLEXIBLE SOURCE WIRE FOR LOCALIZED INTERNAL IRRADIATION OF TISSUE

This is a divisional of U.S. application Ser. No. 08/556,250 filed Nov. 9, 1995 now U.S. Pat. No. 5,833,593.

FIELD OF THE INVENTION

The present invention relates generally to radioactive source wires used to irradiate body tissue in the treatment of disease. More particularly, the present invention relates to the use of an elongated radioactive source wire with increased flexibility for the localized delivery of radiation to diseased tissue.

BACKGROUND OF THE INVENTION

The most common cause of death in industrial countries is ischemic heart disease which, generally speaking, is an imbalance between myocardial oxygen supply and demand. This imbalance is most often due to obstruction of large coronary arteries by sclerotic plaque and is related to either an absolute decrease in coronary blood flow or an inability to increase coronary blood flow relative to the needs of the heart. Ischemic heart disease is most commonly associated with chest pain, an acute heart attack, an abnormal ventricular rhythm and sudden death. Although various medical and surgical therapies may improve the quality of lifestyle of many patients with this disease, these therapies do not favorably change the underlying cause for the coronary vessel narrowing, nor do they stop its progression.

Various medical interventions have been employed to remove or otherwise treat an offending occlusion in the heart including transluminal angioplasty, coronary artery bypass grafting (CABG), balloon angioplasty, stents, and atherectomy. Of these, balloon angioplasty is the procedure of choice and also the least invasive alternative.

In the past, catheters have been developed which may be effectively inserted into blood vessels and maneuvered through a vascular tree. A balloon may be used with such catheters to expand inside the vessel and to open blockages found therein. In a typical percutaneous transluminal coronary angioplasty (PTCA) or percutaneously transluminal angioplasty (PTA) procedure, a guiding catheter is percutaneously introduced into the vascular system of a patient through an artery and advanced therein until the distal tip of the guiding catheter is appropriately positioned. A dilation catheter having a balloon on the distal end thereof and a guide wire are slidably disposed and introduced through the guiding catheter. The guide wire is first advanced through the distal tip of the guiding catheter until the distal end of the guide wire crosses the lesion to be dilated. The dilation catheter is then advanced over the previously introduced guide wire until the dilation balloon on the distal extremity of the dilation catheter is properly positioned inside the lesion. The balloon portion of the dilation catheter is then inflated to a predetermined size to radially compress the atherosclerotic plaque of the lesion against the inside of the artery wall to thereby reduce the annular stenosed area. After a period of time, the balloon is deflated so that blood flow is resumed, allowing the dilation catheter to be removed.

A major problem encountered in a significant number of patients treated by this procedure is the subsequent narrowing of the artery after the expansion treatment. Various methods and apparatus have been developed to address the restenosis problem including multiple inflations of the balloon during the original procedure, atherectomy, hot balloons, and lasers. Even the installation of permanent stents has been thought to potentially have some value in reducing restenosis rates. See, for example, U.S. Pat. No. 5,019,075 to Spears et al. wherein the region surrounding the balloon utilized in the angioplasty procedure is heated by means within the balloon, or within the skin of the balloon, upon inflation of the balloon in order to ideally fuse together fragmented segments of tissue. U.S. Pat. No. 4,733,655 to Palmaz discloses an expansible vascular graft which is expanded within a blood vessel by an angioplasty balloon to dilate and expand the lumen of the blood vessel. The Palmaz method and apparatus leaves the expandable vascular graft in place to ideally prevent recurrence of stenosis in the body passageway.

However, recent data seems to indicate that the prior art methods described above do not significantly reduce restenosis rates of occurrence. It would therefore be desirable to have a method and apparatus to treat a lesion in order to reduce the restenosis rate of occurrence. The present invention is believed to provide a unique method and apparatus to reduce the restenosis rate of occurrence following an angioplasty or like-intended procedure.

As discussed above, percutaneous transluminal coronary angioplasty (PTCA) is now commonly used for opening blockages, also called stenoses, of both peripheral and coronary arteries. However, within a period of several months after PTCA, a significant percentage of treated arteries experience a reoccurrence of the narrowing, also called restenosis, and a seriously reduced blood flow. In fact, clinically evident restenosis occurs in 30–40% of cases following successful PTCA and is most frequently observed between 3 and 6 months after the procedure. Late restenosis in the months after angioplasty reduces the initial success rate of 90% to 60–70% after six months. Although the incidence of success and associated complications has improved significantly over the last decade, the risk of restenosis has not changed. Hence, of the more than 300,000 coronary arteries subjected to angioplasty during 1990, 30–40% can be expected to restenose. As a result, there is a definite need for a method to reduce this high incidence of restenosis.

As the statistics demonstrate, restenosis after PTCA is a serious problem, and to date, there is no treatment to prevent this complication. It appears to be an inherent reaction of the vessel wall to the angioplasty stretching insult. The outward compression caused by the balloon catheter produces cracking, tearing, and stretching of the wall and a subsequent chain reaction of healing events. In short, it is believed to be caused chiefly by the migration and proliferation of smooth muscle cells which produces an exaggerated healing response. This response can progress to the point of severe restenosis and even occlusion. Due to this restenosis, at least one-third of all PTCA patients return for a second and even a third procedure. Accordingly, there is a definite need to decrease this high incidence of restenosis and thereby increase the long-term benefits of PTCA.

Two (2) approaches are currently employed to reduce restenosis. One approach involves the use of a revascularization device, such as the laser catheter, thermal catheter or stent to debulk plaque and create a smooth lumen to minimize turbulence and platelet aggregation along the vessel wall.

Another approach to reduce restenosis involves infusing a drug which modulates cell growth into the target artery before, during, or after the angioplasty to inhibit the profileration of smooth muscle cells. In particular, antiplatelet agents such as aspirin and dipyridamole, and anticoagulants such as heparin, have inhibited platelet aggregation and thrombus formation to a limited degree, thereby reducing the risk of early occlusion. There is therefore a critical need for an effective method to prevent and/or minimize restenosis after an intravascular procedure. The present invention satisfies this need and provides related advantages as well.

Radiation is used to treat cancer and other diseases of the body. Radiation has long been proven to destroy fast multiplying cells (e.g., cancer) in hopes of destroying or preventing the spread of the disease. Brachytherapy, which is the treatment of cancer at close distances, is one example of the use of radiation for treating diseases of the body. During brachytherapy, a radioactive source or sources are positioned in the area needing treatment. Depending on the shape, size and delivery means of the radioactive sources, the sources are either kept permanently in the body or removed after a specific amount of time. Since permanent implants are tiny seeds approximately 3 mm long and 0.5 mm wide, the use of these seeds do not relate to the present invention. Consequently, the focus of this application will be on the field of temporary implants.

The term temporary implants describes the procedure of maneuvering a radioactive source or sources to the treatment site utilizing a transport catheter or tube which has been previously placed in the vicinity of this treatment site. Alternatively, the transport catheter and temporary implant can simultaneously be maneuvered to the treatment site. In either situation, after a specified period of time, these sources and the transport catheter or tube are removed from the body. Since the radioactive source or sources may encounter a tortuous path in various arteries, veins, ducts, or the like inside the body to reach the treatment site, the radioactive source is usually attached by some device to a flexible drive member. This source and the drive member may be used many times, and, therefore must be able to withstand the many bends it encounters when it is maneuvered to the treatment site or removed therefrom, without breaking.

There are several devices on the market in which radioactive sources are attached to flexible drive members. Each of these devices is constructed in a different fashion and each has its limitations. Examples of these prior art devices are described in U.S. Pat. Nos. 4,819,618 and 5,141,486, both issued to Liprie as well as U.S. Pat. No. 4,861,520 issued to van't Hooft. The two Liprie patents describe a radioactive element which is attached to a drive member by means of a junction welded to the drive table. The patent to van't Hooft describes an apparatus which attaches radioactive sources to a drive cable by means of a stiff capsule welded into the end of the cable. Since the most resistive portion to flection of any flexible material, such as a cable, tube, or wire is the segment closest to the end, to join a capsule which is stiffer than this material and welded onto its end would only add to the resistance to bending and would adversely effect maneuvering the material through the body.

U.S. Pat. No. 5,084,002 issued to Liprie describes an ultra-thin high dose iridium source included within an oversized hole drilled inside the end of a solid platinum wire. Drilling a hole into a thin wire is very difficult since the maximum depth the hole can be drilled is equal to approximately seven times the outside diameter of the wire. To drill a hole deeper than this is extremely difficult due to the drifting of the drill as it burrows the hole. This drifting can lead to a thinning of the cavity walls which greatly increases the chances of breakage. This breakage is often disastrous, resulting in unwarranted radiation exposure. A larger outside diameter wire will be needed to compensate for the drifting and still allow the walls of the cavity to be thick enough to withstand stress. Unfortunately, this larger diameter wire might be too large to fit into many constricted areas of the body. As described in Liprie '002 one can drill a cavity inside a solid wire, if one starts with an oversize wire and an oversize hole and then the whole assembly is drawn down to the desire diameter of the wire. However, whenever a wire is drawn down, the assembly containing the cavity elongates and the precise positioning of the radioactive core inside the assembly can become very difficult. Additionally, this larger diameter wire would result in less flexibility and may not be able to be maneuvered to the treatment site.

Finally, U.S. Pat. No. 5,282,781 issued to Liprie employs tube, a backbone wire, a pure iridium core and a plug and draws down the entire assembly to form a tight seal between the housing material and the backbone wire and the plug. Without this drawing down of the housing onto the backbone wire, radioactive flakes from the core would migrate throughout the inside of the assembly wire, resulting in unwanted contamination. This "drawing down" step would increase the costs and difficulty of manufacturing the source wire. Furthermore, any "drawing down" step as described in U.S. Pat. No. 5,084,002 and U.S. Pat. No. 5,282,781 would not work on a memory resistant alloy. As soon as a memory resistant alloy had been drawn through a die, the alloy would resume its original shape. If the memory resistant alloy was drawn beyond the threshold of its elasticity, then the memory resistant properties of the alloy would be destroyed.

Thus, there exists a need for a radioactive source wire that has an extremely small diameter and is flexible, yet has sufficient tensile strength to traverse a tortuous route of bends and turns without breaking.

It is an object of the present invention to provide a small diameter source wire that is extremely flexible and will allow the source to travel to the site of treatment without binding.

It is another object of the present invention to provide a source wire that is strong enough to withstand the stresses placed upon the source, as it is maneuvered to and from the site of treatment within the patient, without breaking.

Yet another object of the present invention is to provide an improved source wire design that includes a mechanism for relieving some of the stress encountered by the metal housing tube of the source wire as it is maneuvered to the treatment site.

Still yet another object of the present invention is to provide an improved source wire that exhibits little or no memory retention when bent.

SUMMARY OF THE INVENTION

These and other deficiencies of the prior art are addressed by the present invention which is directed to a flexible source wire for the radiation treatment of disease in which the source wire contains a radioactive core and is easily maneuvered to the site of treatment through various conduits in the body.

One general embodiment of the source wire of the present invention includes a thin, generally cylindrical, elongated, flexible housing tube having a distal end and a proximal end. The housing tube further comprises an unmodified section at its distal end and a modified segment at its proximal end, where the wall thickness of the modified segment is thinner than the wall thickness of the unmodified section. A plug seals the lumen of the unmodified section from the lumen of the modified segment which contains a radioactive core.

Both ends of the source wire are sealed and at least the proximal end is rounded to ease its movement through the tortuous bends and turns as it travels to the treatment site.

An alternative embodiment of the source wire has a tapered section, having a tapered internal diameter that goes from the larger internal diameter of the modified segment to the smaller internal diameter of the unmodified section. Other embodiments may also include a backbone wire that extends throughout the unmodified section to the tapered section. Preferred embodiments of the present invention will have a housing tube and a plug constructed from a material exhibiting little or no memory retention when bent.

The flexible source wire described herein may have a backbone wire or plug that is tapered at the end closest to the radioactive core. The tapered end of the backbone wire or plug terminates next to the radioactive core in a rounded area shaped like a ball. The radioactive core, positioned within the proximal end of the housing tube, may exist openly within the housing tube or may be localized in an open-ended capsule or may be encapsulated by a thin-walled, flexible material or coating that allows the passage of neutrons.

One advantage of the present invention is that it can be made with a smaller diameter housing tube than the source wires that are currently available.

Another feature and advantage of the present invention is that the source wire has a sufficient tensile strength and flexibility to withstand the stresses encountered when the source wire is maneuvered to the site of treatment.

Yet another feature and advantage of the present invention is that it provides a novel mechanism for transferring the stress encountered by the metal housing tube as the source wire is maneuvered to the treatment site from the weakest portion of the source wire to the strongest portion of the source wire.

Still yet another feature and advantage of the present invention is that the source wire is made of a material that can undergo a 1% strain with less than a 1% alteration in its original conformation.

Another feature and advantage of the present invention is that the source wire will exhibit flexibility similar to a tube and have the tensile strength properties closer to a solid wire.

An additional feature and advantage of the present invention is that the radioactive source is visible with a fluoroscope.

Another feature and advantage of the present invention is that the radioactive material of the radioactive source is sealed within the proximal end of the source wire.

Still yet another feature and advantage of the present invention is that the radioactive source is long enough to treat the entire length of an angioplasted vascular stenosis.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 is a partial cross-section of one embodiment of a source wire having a housing tube with a thicker walled unmodified section, a thinner walled modified segment, a plug between the modified and unmodified sections and a radioactive core all enclosed within the housing tube;

FIG. 2 is a partial cross-section of another embodiment of a source wire having a housing tube with a thicker walled unmodified section, a thinner walled modified segment, a tapered section adjoining the modified and unmodified sections, a plug between the modified and unmodified sections and a radioactive core all enclosed within the housing tube;

FIG. 4 is a partial cross-section of another embodiment of a source wire illustrating an alternative embodiment of the plug;

DETAILED DESCRIPTION OF THE PREFERRED EMBODIMENTS

Figure 3A:
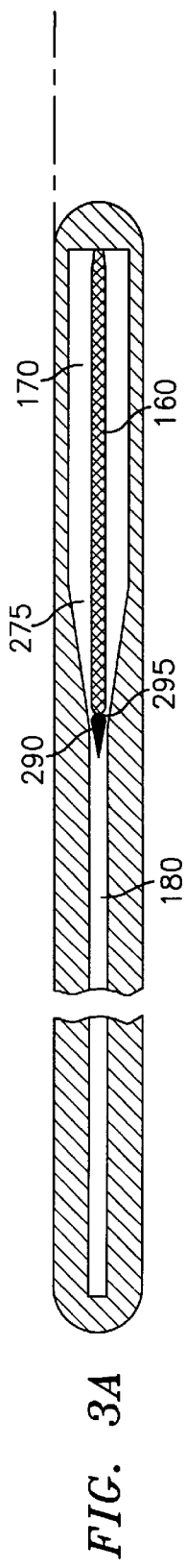
FIG. 3A shows the embodiment of the source wire illustrated in FIG. 2 in an unstressed, state.

The present invention relates to the design and manufacture of improved source wires for delivering radioactivity to a site of treatment within a human or animal body. The invention relates to a novel source wire design that provides improved source wire flexibility and strength such that the improved source wire can survive the stress encountered when it is subjected to the manipulations necessary to maneuver the source wire to and from an internal treatment site for the localized delivery of radiation to diseased tissue. The present invention may be used to treat cancer, stenosis, or other diseases of the body. The use of the present invention in the treatment of stenosis is described in co-pending U.S. patent application entitled "Method and Apparatus for Treating Stenosis," Ser. No. 08/220,681, and is hereby incorporated by reference herein.

Referring now to the drawings, and initially to FIG. 1, it is emphasized that the Figures, or drawings, are not intended to be to scale. For example, purely for the sake of greater clarity in the drawings, wall thickness and spacings are not dimensioned as they actually exist in the assembled embodiments. Furthermore, the lengths of the backbone wire and the radioactive core are illustrated out of proportion to how they actually exist, purely for the sake of clarity.

FIG. 1 illustrates a first embodiment of a source wire 10. Among the components of the source wire 10 is an elongated, flexible metal housing tube 120. Since this housing tube 120 is used to maneuver the radioactive core to a remote treatment site, the length of the tube must be adequate to reach the treatment site when the source wire 10 is inserted through a catheter implanted in a patient's body for that purpose. Typically, tube 120 will have a length of at least 100 cm and may extend for a much greater distance.

Selecting the size of the outside diameter of the metal housing tube 120 requires that one balance the increased trauma to the tissue through which source wire 10 will pass caused by larger diameter tubing, with the increase in tensile strength and elongation of larger diameter tubing. The tubing to be used should be as small as practical and still have the tensile strength, flexibility, and elongation properties necessary to withstand the pressures put upon the source wire while it is maneuvered throughout the body. The outside diameter of housing tube 120 will typically range from about 0.012" to about 0.018" and is preferably about 0.014".

Although any type of metal tubing can be used, a preferred housing tube 120 is constructed from a material that can accept up to a 1% strain with less than a 1% alteration in its original shape (i.e., a material that exhibits little or no memory retention when bent). Most metals such as stainless steel will incur a permanent alteration in shape when subjected to as little as a 0.1% strain. An example of a material that exhibits little or no memory retention when bent is Tinel Alloy BB, a titanium/nickel alloy, manufactured by Raychem Corporation, Menlo Park, Calif. Another commercially available alloy with similar properties is Nitinol® manufactured by Shape Memory Alloys, Sunnyvale, Calif. Tinel Alloy BB, and other such nickel/titanium alloys, are comprised of about equal quantities of nickel and titanium, such as an alloy composed of about 55% nickel and about 45% titanium.

Tube 120 has two ends, one of which will ultimately constitute the proximal end 140 and the other the distal end 150 of source wire 10. The distal end 150 of tube 120 may be sealed in any number of ways. The proximal end 140 should be rounded to facilitate the movement of source wire 10 through the bends and turns of the vasculature, or other treatment sites.

Preferred embodiments of housing tube 120 will have an internal diameter that is 25 to 60% of the outside diameter. Commonly an internal diameter is selected that is 0.008" smaller than the outside diameter. The internal diameter will vary according to the external diameter of the tubing used. For example, tubing that has an external diameter of about 0.012" will commonly have an internal diameter of about 0.004" while tubing having an outside diameter of about 0.018" may have an internal diameter of about 0.010".

Housing tube 120 will be modified at its proximal end to accept a radioactive core 160, described below. A short segment of housing tube 120, said segment at least the length of radioactive core 160, will have material removed from the inner surface 130 of housing tube 120 to create a modified segment 170. Typically at least 0.002" of material will be removed from the inner surface 130 of housing tube 120 by grinding, reaming, drilling, laser boring, or similar methods. Preferred embodiments have an internal diameter of modified segment 170 that is about 0.004" wider than the internal diameter of the unmodified section 180 of tube 120 and the wall thickness of the modified section will be at least 0.002" thinner than the wall thickness of the unmodified section of tube 120.

The increased wall thickness of unmodified section 180 makes that section the strongest section along the length of the source wire 10. Despite the wall thickness and strength of the unmodified section 180, its lumen allows the housing of unmodified section 180 to temporarily give and flex inward, thus source wire 10 takes advantage of a tube construction.

Modified section 170 has a thinner wall thickness and is more flexible than the unmodified section 180. Removal of material from the inside diameter of the proximal end of tubing 120 to provide a thinner wall along modified segment 170, will substantially increase the flexibility of modified segment 170. This increased flexibility at the front end of the source wire will allow the source wire to maneuver easier through tight bends and curves.

A second component of source wire 10 is plug 190. Plug 190 provides a seal between modified segment 170 and the unmodified section 180 of tube 120. Plug 190 serves to keep all radioactivity, including any radioactive flakes or oxidized material issuing from radioactive core 160, from entering the lumen of unmodified section 180. Thus, plug 190 serves to contain all radioactivity within the proximal end of source wire 10. One advantage in containing all radioactivity within a short segment of the source wire (e.g., within modified segment 170) is that only this short segment of the source wire must be disposed of as radioactive waste, thereby decreasing the storage requirements for radioactive waste.

A preferred embodiment of plug 190 has a rounded surface 195 facing the proximal end of tubing 120 which abuts radioactive core 160 as seen in FIG. 1. The rounded end 195 allows for greater pivoting of the source wire assembly while reducing stress on the housing material.

A third component of source wire 10 is a radioactive core 160. Radioactive core 160 may be composed of a variety of different radioisotopes, some of which are Ir-192, Cs-137, Co-57, Co-60, Sr-89, Sr-90, P-32, Y-90, Au-198, I-125, Pd-103, Se-75, or Ru-106. However, the preferred embodiment of core 160 will consist of a substantially pure iridium, which has been irradiated in a nuclear reactor to produce Ir-192 of a predetermined strength appropriate to its weight.

Preferred embodiments of the present invention have a radioactive core 160 that is flexible and has rounded ends to allow pivoting and bending of the core 160.

A preferred embodiment of the invention has a radioactive core 160 that is at least 20 mm in length and emits approximately 380 keV of energy. By spreading out the 380 keV emitted over at least a 20 mm distance, core 160 is directly visible with a fluoroscope. Although the energy emitted by radioactive core 160 and the length of the source of radioactivity will vary with different embodiments of the invention, the preferred embodiment will have a radioactive core that can be seen with a fluoroscope. This feature provides a distinct advantage over the source wires that are currently available that have a radioactive iridium core of 10 mm or less in length. These point sources emit the equivalent 380 keV of energy in a less diffused manner. Thus the emitted energy hits the fluoroscope directly and overrides its ability to visualize the radioactive source. Therefore, the radioactive cores of currently available source wires are not directly visible with a fluoroscope and must be positioned inside the body without the visual confirmation allowed with the present invention.

Point sources also require a technique called "microstepping" in order to treat bodily diseases. Point sources consist of a radioactive core that is very short in length (often just a few millimeters long) and contain a highly concentrated amount of radioactive material. This type of source must sit precisely in one position for an exact amount of time and then be either retracted or advanced the length of the radioactive core to treat the next segment of the diseased tissue. When the point source of radioactive material is much shorter than the length of the desired treatment area, treatment of the diseased tissue must occur in "microsteps" in order to treat the entire length of the diseased tissue. A major problem associated with having to treat the diseased tissue in micro-steps particularly when the treatment site is in an area of the body that is constantly in motion such as the coronary system, is that precise alignment of the point source to a particular treatment site is not possible. Parts of the diseased tissue will not be treated adequately, while other parts will receive too high a radiation dose creating a very dangerous situation. The preferred embodiment of this invention has a radioactive core length greater than or equal to 20 mm, with the radioactivity evenly spread over the entire core length. Thus, the entire diseased tissue can often be treated with a single placement of the radioactive source, thus eliminating the need to micro-step a highly concentrated point source. Use of this invention will allow a much safer and more precise treatment to be given.

Core 160 has a diameter that is smaller than the inner diameter of modified segment 170 and larger than the inner diameter of unmodified section 180. A preferred embodiment of the invention has a core 160 that is about 0.0051" in diameter. Core 160 will preferably have a diameter ranging from about 0.003" to about 0.009" depending on the outside diameter of the housing tube 120. Core 160 is inserted in the proximal, end of the lumen of tube 120 and is pushed inward until core 160 abuts plug 190 or the proximal end 185 of the unmodified section 180 of tube 120. A plurality of radioactive cores 160 may also be employed in the present invention.

Once the core 160 has been inserted into source wire 10 the proximal end 140 of tube 120 is sealed by any number of methods known to one skilled in the art. A preferred embodiment will seal and round proximal end 140 using an arc welder, such as a tungsten inert gas (or TIG) welder. The purpose of the rounded end of source wire 10 is to facilitate the advancement of the source wire 10 through an implanted catheter to the treatment site.

FIG. 2 illustrates a second embodiment 20 of the present invention. This embodiment is similar in many respects to the embodiment shown in FIG. 1 and will have the same reference numerals as the respective elements pictured in FIG. 1. This embodiment also has an elongated cylindrical metal housing tube 120, similar in dimensions and characteristics to the tube described with respect to FIG. 1. The embodiment of the source wire shown in FIG. 2 has a tapered section 275 which adjoins unmodified section 180 on its distal end and modified segment on its proximal end. Tapered section 275 can be created using a tapered reamer, a tapered drill bit, a series of drill bits, a series of EDM probes, or a series of laser probes so that a portion of the inner surface 130 will be reconfigured to taper from the larger internal diameter of modified segment 170 to the smaller internal diameter of the unmodified section 180 of tube 120. Tapered section 275 will typically be at least five (5) millimeters long.

Internal taper 275 allows the source wire to bend several degrees before stress is applied to the housing of tube 120 by the radioactive core 160. Even when the wire bends sufficiently to apply stress to the tube housing, the design of source wire 20 will allow the stress on the housing material to be transferred from its weakest area (i.e., the modified segment 170 with its thinner wall) to its strongest area (i.e., the unmodified section 180 with its thicker wall) as shown in FIGS. 3A–3D.

Figure 3B:
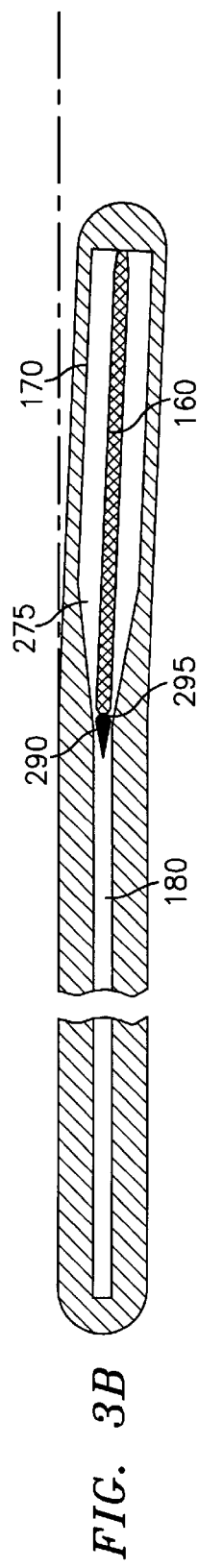
FIG. 3B shows the tapered segment allowing the source wire assembly to pivot or start a turn without stress being applied to the thin-walled modified segment of the source wire.
Figure 3C:
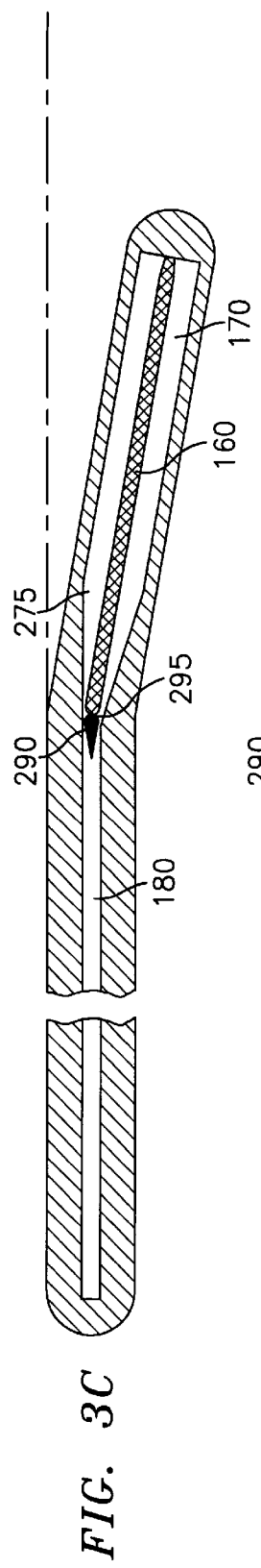
FIG. 3C shows how the tapered segment transfers the stress from the thin-walled modified segment to the thicker walled unmodified section of the source wire as the source wire negotiates a tighter turn.
Figure 3D:
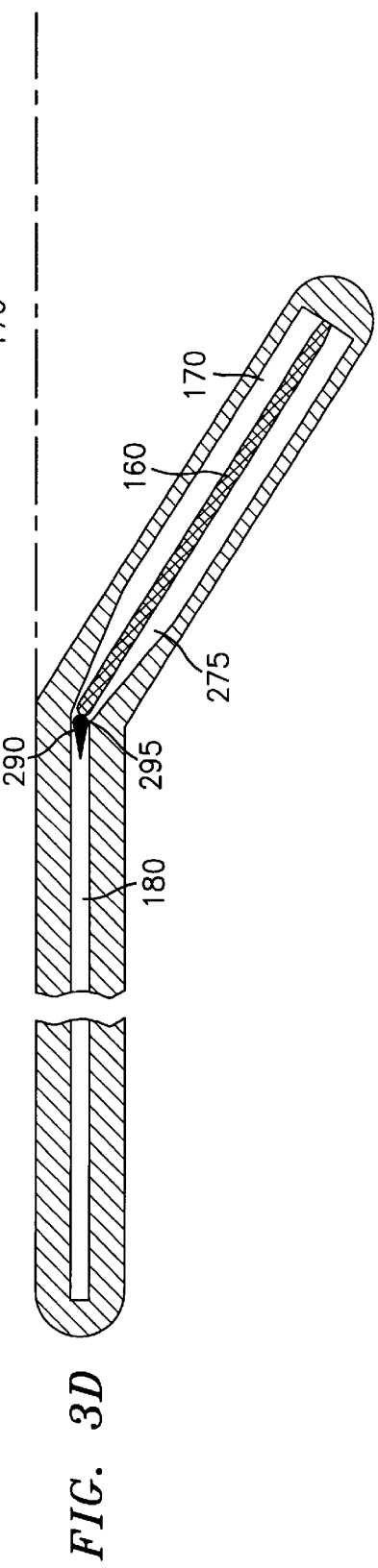
FIG. 3D shows how the tapered segment allows the stress to be transferred to the thicker walled unmodified section o the source wire as the source wire negotiates a very tight turn.

FIG. 3A shows one embodiment of the source wire in an unstressed state. FIG. 3B illustrates how tapered section 275 and modified segment 170 allow radioactive core 160 to pivot about the rounded end 295 of plug 290 when the source wire enters a turn without applying stress to the thinner walled modified segment 170. FIGS. 3C and 3D illustrate how the tapered section 275 allows the stress to be transferred to the thicker walled unmodified section 180 as the source wire negotiates tighter and tighter turns. This novel design feature not only increases the flexibility of the proximal end of the source wire but it also adds to the stability of the source wire by making it less likely to break at the proximal end where the radioactive core is located.

Plug 290 provides a seal between unmodified section 180 and tapered section 275. Plug 290 has one end that fits into the lumen of unmodified section 180 and another end that is rounded and abuts radioactive core 160. This rounded end 295 allows the greater pivoting of the source wire while reducing stress on the housing material as illustrated in FIGS. 3A–3D.

FIG. 4 shows another embodiment of the plug used to seal the end of the lumen of the unmodified section 180 from radioactive materials. Plug 490 is situated at or about the junction of the unmodified section 180 and the tapered section 275. Plug 490 does not necessarily have a rounded edge as is seen in the preferred embodiments. However, plug 490 can be easily and inexpensively implanted, as for example, by using a long needle to inject an epoxy glue into the proximal end of the lumen of unmodified section 180. Plug 490 may also be a flexible seal composed of a flexible material such as latex that has been glued in place at or about the junction of unmodified section 180 and tapered section 275.

Figure 5:
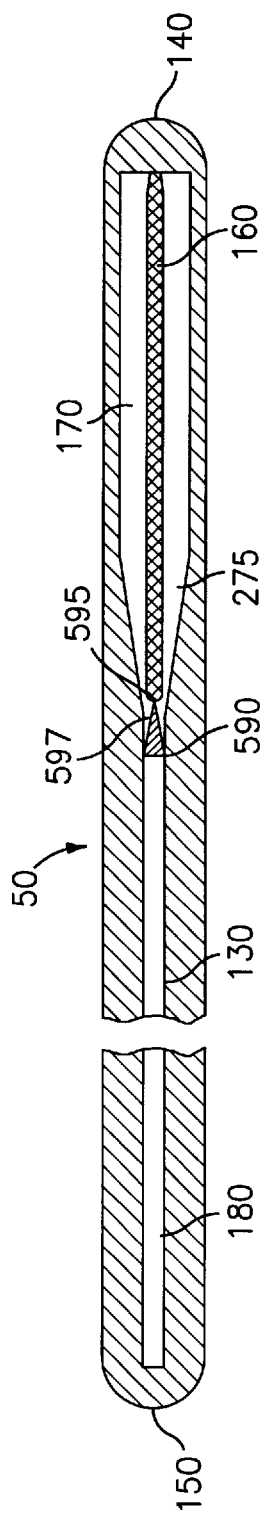
FIG. 5 is a partial cross-section of another embodiment of a source wire illustrating yet another alternative embodiment of the plug.

Plug 590, illustrated in FIG. 5, is made of a memory resistant material such as described above. Plug 590 is attached to the inner surface 130 of the unmodified section 180 and extends into the distal end of tapered section 275 where it abuts radioactive core 160. Plug 590 is tapered as it extends towards the radioactive core and terminates in a rounded area 595 approximating the shape of a ball. A preferred embodiment of taper 597 goes from a 100% width where plug 590 is attached to the unmodified section 180 to a width that is from about 30% to 70% of that width where the tapered portion of plug 590 is attached to rounded area 595.

This configuration keeps rounded area 595 and radioactive core 160 suspended within the tapered section 275 of housing tube 120. By maintaining a space between the inner wall of the tubing and the radioactive core 160 and plug 590, source wire 50 can take advantage of the full flexibility of the tapered section 275 without interference from either plug 590 or radioactive core 160. However, the space left between the inner wall of tubing 120 and rounded area 595 is insufficient to allow radioactive core 160 to pass beyond the rounded area 595 into the lumen of unmodified section 180.

The design of source wire 50 allows it to release some of the stress on the outer wall of housing tube 120 whenever the source wire bends to traverse a tight corner. The stress placed on the rounded area 595 will cause the tapered portion 597 of plug 590 to crumple. However, if plug 590 is made of a memory resistant material then plug 590 will resume its original shape when the stress is removed from the rounded area 595.

Figure 6:
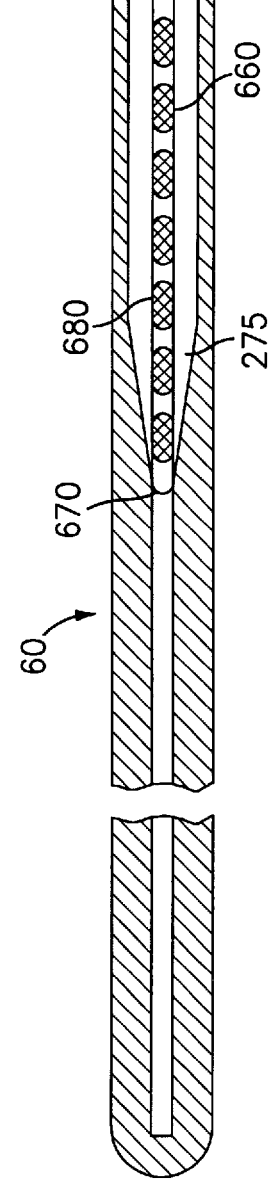
FIG. 6 is a partial cross-section of another embodiment of a source wire without a plug and where the radioactive core is encapsulated in a neutron permeable material.

FIG. 6 shows yet another embodiment of the present invention. The source wire illustrated in FIG. 6 contains a plurality of radioactive cores 660 enclosed in a thin-walled capsule 680. Capsule 680, illustrated in FIG. 6, surrounds the radioactive core and will function to contain all radioactive material within the capsule. Alternatively, radioactive core(s) may be placed in an open-ended capsule (not illustrated herein). If an open-ended capsule is used the open end would face the proximal end of the source wire.

The radioactive core(s) are located in the capsule inserted into tube 120 so that the distal end 670 of the capsule 680 lies at or near the intersection of the unmodified section 180 and the tapered section 275. When the radioactive core is enclosed in a capsule, the plug is not needed to prevent any radioactive material from entering the lumen of the unmodified section.

Capsule 680 should be flexible and thin. The wall of capsule 680 must be made of a material that allows the passage of neutrons without obtaining significant radioactivity itself. If the capsule material should become radioactive by neutron flux, the material and any contaminants of that material should have a short half-life as compared to the radioactive core. It is important that the capsule 680 should emit less than 10% of the radiation emitted by radioactive cores 660.

The capsule may be made in a variety of ways. For example, it may be made from a carbon filament sealed with epoxy at both ends, or it may be a very thin metallic substance (e.g., titanium, a high purity aluminum such as aluminum 1100, platinum, or the titanium/nickel alloy described previously) with both ends welded, soldered, or glued closed. In a preferred embodiment the iridium will be encapsulated before it is irradiated to form Ir-192 and the capsule 680 will allow the passage of neutrons to irradiate the core.

The preferred embodiment of capsule 680 will be rounded on both ends. The purpose of having a rounded distal end 670 of capsule 680 is to allow greater pivoting of the source wire 60 while reducing stress to the housing material. Although the preferred embodiment has a single capsule 680, a plurality of capsules could be employed in the present invention, or a plurality of cores 660 could be incorporated within a single capsule 680 as shown in FIG. 6.

One alternative to capsule 680 that is not shown would be for radioactive core 660 to have a thin coating of a neutron permeable material. The coating may be an electroplated coating of a material such as gold, titanium, platinum, etc. The coating may also be made of a non-metallic material such as a hardening agent (e.g., glue or acrylic). The coating may be applied to core 660 by brushing, dipping, painting or molecularly bonding the coating material to the outer surface of core 660.

Figure 7:
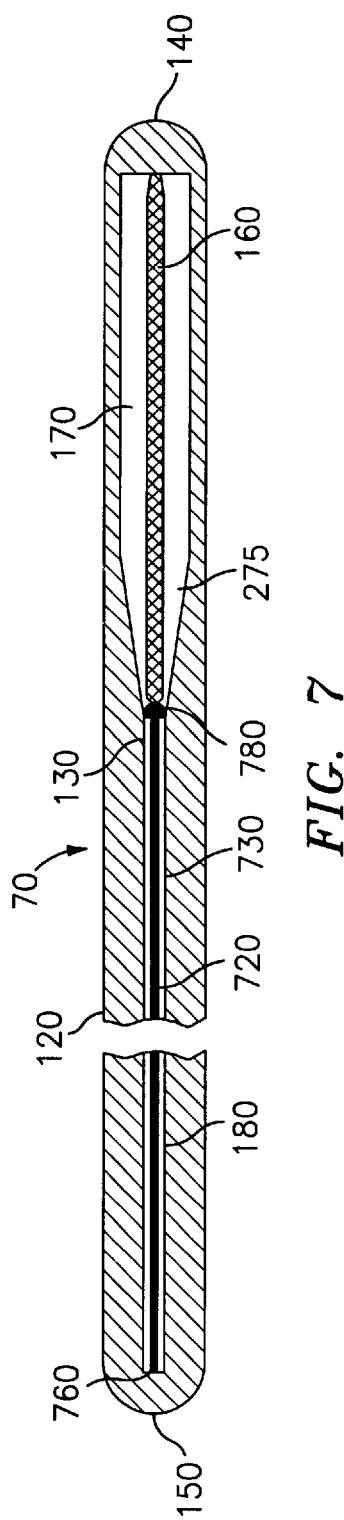
FIG. 7 is a partial cross-section of another embodiment of a source wire having a flexible backbone wire running throughout the entire unmodified section of the housing tube.

FIG. 7 illustrates a preferred embodiment of the present invention. This embodiment of a flexible source wire 70 is similar in many respects to the other embodiments of the present invention. Therefore the elements in FIG. 7 corresponding to similar elements in the previous figures will be given the same reference numerals as their respective elements in the previous figures. Source wire 70 contains an optional flexible backbone wire 720, as illustrated in FIG. 7, which has a diameter slightly less than the inner diameter of unmodified section 180, and is preferably about 0.001" smaller in diameter than the internal diameter of unmodified section 180. Backbone wire 720 is positioned within the lumen of unmodified section 180 from the distal end 150 to the tapered section 275 of tube 120. The distal end of the backbone wire 720 will generally be secured to the distal end 150 of housing tube 120 by weld 760, or some other means of attachment such as gluing. The proximal end of backbone wire 720 has a rounded end 780 that is larger than the lumen of the unmodified section 180 and extends into tapered section 275 where it abuts the radioactive core 160.

An important function of backbone wire 720 is to increase the strength of source wire 70 without reducing the flexibility of source wire 70. The backbone wire 720, like the housing tube 120, is composed of a very flexible material with sufficient tensile strength to undergo the stress encountered when the source wire 70 is maneuvered to a treatment site. Therefore, backbone wire 720 should be constructed of a material with properties similar to that of housing tube 120. In fact, if the backbone wire 720 is welded to the distal end of tube 120 then the backbone wire 720 and tube 120 should be made of the same material, such as a titanium/nickel alloy as described above.

Another important function of backbone wire 720 is to serve as a safety mechanism. Since rounded end 780 fits against the proximal end of unmodified section 180 and is too large to fit within the lumen of unmodified section 180 while the other end of backbone wire 720 is attached to the distal end 150, backbone wire 720 will prevent the radioactive core from separating from the rest of the source wire 70 even if the housing tube 120 were to break anywhere along the unmodified section 180. It is important that the radioactive core 160 remain attached to the distal end of the source wire so that it will be retracted from the patient when the source wire is withdrawn from the patient.

Alternative embodiments of backbone wire 720 may extend into the tapered section 275 such that the rounded end 780 will suspend radioactive core 160 within the tapered section 275. This embodiment of the backbone wire, like backbone wire 820 illustrated in FIG. 8, may be affixed to the inner surface 130 of housing tube 120 at a variety of attachment sites 830 to prevent the migration of radioactive material into the unmodified section 180. The backbone wire may be attached to the inner surface 130 by welding, fusing, soldering, gluing, etc. Attachment sites 830 may also provide an internal safety device that insures if housing tube 120 were to break at any point distal to an attachment site that the radioactive core 160 would not separate from the backbone wire and could be retracted from the patient.

Backbone wire 820 has a proximal end that is configured like plug 590 with a tapered area 897 and a rounded area 895. The proximal end of backbone wire 820 thus provides all of the advantages discussed for plug 590.

Figure 9:
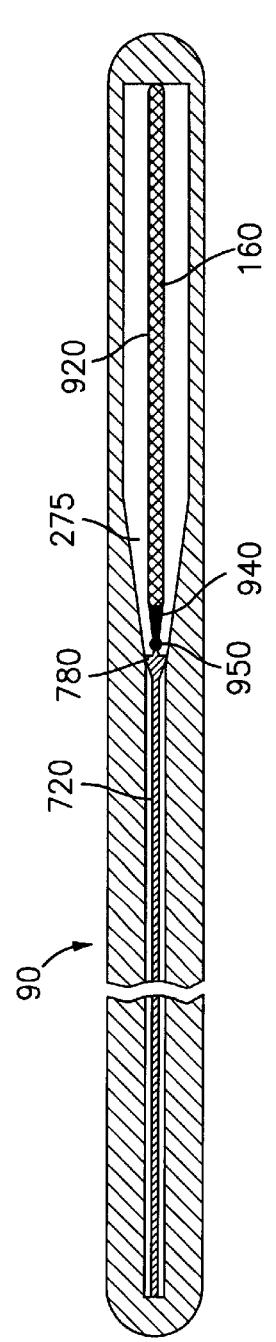
FIG. 9 is a partial cross-section of another embodiment of a source wire illustrating an alternative embodiment of an encapsulated radioactive core.

FIG. 9 illustrates a source wire 90 that is very much like source wire 70, except that radioactive core 160 is encapsulated in a thin-walled capsule 920 of a neutron permeable material. Capsule 920 differs from capsule 680 in that its distal end that abuts the rounded end 780 of backbone wire 720 has been extended to include a tapered area 940 and a rounded area 950. This configuration of capsule 920 increases the flexibility of source wire 90 at the junction of backbone wire 720 and the distal end of capsule 920 thereby increasing the flexbility of source wire 90 at tapered section 275. Preferably radioactive core 160 will be encapsulated in capsule 920 before the radioactive core is sent to a nuclear reactor for activation.

Many combinations of the elements described in the illustrative examples above are possible. For example, elements of source wire 90 may be integrated into a source wire with elements of source wire 50 or 80. All such permutations and variations are within the scope of the appended claims.

An optional feature of all the source wires described herein (but not shown) would be to coat the exterior surface of the source wire with a non-oxidizing agent, such as gold. In one embodiment of the present invention, a thin gold layer (from approximately 1 to 10 microns thick) would be electroplated over the outer surface of metal housing tube 120, or at least that portion of the surface overlying the radioactive core 160 and preferably over the proximal end of the source wire. Furthermore, the gold coating of the source wire would preferably be done prior to loading the radioactive core 160 into the modified segment 170 of housing tube 120.

The fabrication of the source wires shown in FIGS. 1–9 above is described below. The first step in the manufacture of the described source wires is to obtain the metal tubing that will be used to make housing tube 120. Once the tubing is acquired, a calibrated micrometer for measuring the outside diameter and calibrated rods for measuring the inside diameter are used to validate that the tubing meets the manufacturer's specifications. The present invention can be made from any type of metal tube, however, the preferred embodiments are made from memory-resistant materials (i.e., materials that can accept up to a 1% strain with less than a 1% permanent alteration in its original configuration). The preferred embodiment of the present invention uses Tinel Alloy BB tubing having an external diameter of 0.014" from Raychem Corporation. Housing tube 120 is constructed of a hollow tube with an inside diameter at least 0.001" smaller than the outside diameter of the radioactive core 160, or encapsulated core.

A second step in the manufacture of the source wire is to modify the proximal end of the tubing to accept the radioactive core 160. A short segment of housing tube 120, said segment at least the length of radioactive core 160, will have material removed from the inner surface 130 of housing tube 120 to create a modified segment 170. Typically at least 0.002" of material will be removed from the inner surface 130 of housing tube 120 by grinding, reaming, EDM, drilling, laser boring, or similar methods. Thus, the internal diameter of modified segment 170 will be at least 0.004" wider than the internal diameter of the unmodified section 180 of tube 120 and the wall thickness of the modified section will be at least 0.002" thinner than the wall thickness of the unmodified section of tube 120.

Approximately five (5) millimeters of-tubing 120, distal to the modified segment 170 may optionally be tapered. Tapered section 275 can be created using a tapered reamer, a tapered drill bit, a series of drill bits, a series of EDM probes, or a series of laser probes so that a portion of the inner surface 130 will be reconfigured to taper from the larger internal diameter of modified segment 170 to the smaller internal diameter of the unmodified section 180 of tube 120. Tapered section 275 will typically be at least five (5) millimeters long.

As material is removed from the inner wall of tubing 120 it may be necessary to periodically flush the tubing with pressurized air or liquid, or to run a backbone wire from the distal end of the tubing out the proximal end to help remove any loose material that accumulates during the removal process. The end result will be a cavity wide enough and long enough to house the entire length of the radioactive core plus at least one (1) millimeter. The distal end of the cavity may contain a tapered section 275 going from the larger inside diameter, is housing the radioactive core, to the smaller original inside diameter of the tubing.

When the radioactive core 160 is inserted into the proximal end of the source wire it may extend into the tapered section 275. A gap should exist between the walls of the tapered section 275 and the outside diameter of the radioactive core 160. If the cavity is accidentally made too long, the modified segment 170 may be shorten by grinding, sanding, filing, or similar means until the correct overall dimensions are achieved.

If a non-memory resistant material (a material where a 1% strain results in at least a 1% permanent alteration in its original configuration) is used, then different methods can be used to produce the required dimensions of the tubing and the cavity for holding the radioactive core 160. Non-memory resistant tubing can be reduced in size to the proper inside and outside diameter by employing either swaging, drawing down, or a combination of both, using a series of removable mandrels and diamond dies. A removable mandrel would be placed inside the tubing and the tubing would be drawn down or swaged forward through a diamond die to a point prior to the required inside taper, to achieve the proper outside diameter and inside the diameter of this length of tubing. A tapered removable mandrel with the proper diameter would now be placed in the remaining portion of the tubing and the tubing would be swaged forward or drawn down through the die creating the required dimensions of the taper and cavity within the proximal end of the tubing 120. The use of a split die or a die that can break apart and be clamped back together, allows precise positioning of the removable mandrels. If the cavity of the tubing is too long, the proximal end may be shorten by grinding, sanding, filing, or similar means until the correct overall dimensions are achieved.

If necessary, several methods involving grinding, polishing, honing, and/or glazing can be applied to the inner walls of the modified segment 170 and tapered section 275 to seal any breaks in the integrity of housing tube 120 and to remove any micro-cracks or micro-voids that might be present due to the removal of the inner wall material:

1) polishing, honing, or grinding can be accomplished by the use of a rotating rod (or tapered rod) encrusted or coated with a very fine abrasive;
2) glazing can be accomplished by using a heated rotating rod (or tapered rod) with or without abrasive; or
3) glazing may be accomplished using a laser fiber.

These are a few examples of ways to remove micro-voids or micro-cracks to inner wall material. Any other method such as coating the inner wall material with a thin layer of a flexible hardening or bonding agent or any method that achieves the same result may also be used.

An optional backbone wire would then be obtained commercially. A preferred embodiment of backbone wire 720 is a solid wire of Tinel Alloy BB with a diameter of about 0.003". Rounded end 780 of backbone wire 720 is produced using the heat from a TIG welder. Once rounded end 780 has been formed, backbone wire 720 will be threaded from the proximal end of tube 120 towards the distal end of tube 120 until rounded end 780 reaches the proximal end of the unmodified section 180. Since rounded end 780 cannot enter the lumen of the unmodified section 180, backbone wire can be secured by cutting the wire where it extends from the distal end of tube 120 and welding the distal end of the backbone wire 720 to the distal end of tube 120. If the backbone wire and the tube are not constructed of the same material, the distal ends of the wire and the tube may be joined using a number of other methods known in the art.

Figure 8:
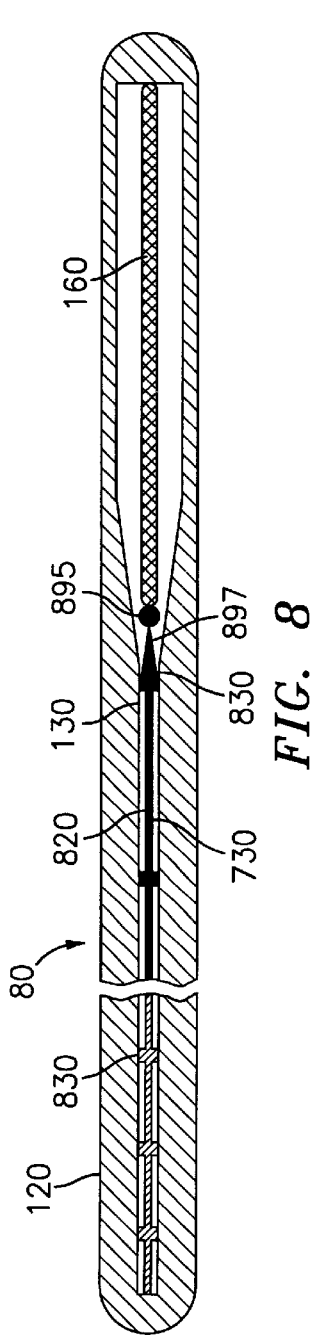
FIG. 8 is a partial cross-section of another embodiment of a source wire illustrating an alternative embodiment of a backbone wire.

The alternative embodiment of a backbone wire illustrated in FIG. 8 (backbone wire 820) is made by taking the Tinel Alloy BB wire ordered and grinding it down with an electric sander. The wire is held in a pin vise and rotated while grinding to taper the wire. The tapering can be done automatically or manually. The tapered end is examined under a microscope and with a micrometer to ensure that it is tapered sufficiently (i.e., with the right degree of reduction in the diameter of the wire and that it is evenly tapered). Once the appropriate taper of backbone wire 820 is achieved then the rounded area 895 is formed on the tapered end of backbone wire 820. The rounded area 895 is formed by heating the tapered end of backbone wire 820 with an arc welder after placing the tapered end of backbone wire 820 into a heat sink (preferably made of aluminum, copper, brass, or any other material that will absorb heat away from the protected object) at a predetermined distance above the heat sink. The dimensions of the rounded area 895, or ball, will be determined by the gap between the top of the wire and the bottom of the tungsten welding rod and by the length of the wire above the heat sink that is exposed to the heat of the TIG welder. Typically the backbone wire is placed 0.025" (or about 0.1 mm) above a heat sink using a feeler gauge. A feeler gauge is also used to set a gap of about 0.030" between the top of the backbone wire and the bottom of the welding rod. Once the tapered end of backbone wire 820 is placed the proper distance from the heat sink and the welding rod, the tapered end of backbone wire 820 is exposed to a TIG welder. The metal above the heat sink will melt and form a rounded area 895. Typically, the rounded area will be a ball of about 0.003" in diameter, or of a similar diameter as the untapered backbone wire.

Next the backbone wire is inserted into the housing tube 120. For example, to insert backbone wire 720 (smaller in diameter than the inside diameter of the modified section 170) with a rounded end 780 too large to fit into the lumen of the unmodified section 180, but small enough to fit into the tapered section 275, one would start with a backbone wire that is slightly longer than the length of the tubing 120. The non-rounded end should be advanced from the proximal end of tubing 120 until it exits out the distal end. The wire is then pulled from the distal end until the rounded end is flushed with proximal end 140 of tubing 120. A mark is placed on the distal end of the backbone wire at the point where it exits the tubing. The backbone wire is then pulled distally until the mark is at a distance away from the distal end of the tubing equal to at least the length of the radioactive core 160 plus one millimeter. To determine if the rounded end 780 is properly seated, a thin measuring wire is inserted from the proximal end until it touches the rounded end 780 of backbone wire 720. A mark or tape is placed on the measuring wire at the point where the wire is exiting the tubing. The measuring wire is removed and placed on a calibrated ruler to determine the proper distance. If the backbone wire is not properly seated, it will need to be pulled deeper into the tubing or advanced out towards the proximal end if it is seated too deep. If it can not be advanced any deeper due to the diameter of the rounded end 780, the diameter of the rounded end 780 can be reduced by lightly grinding or sanding it until it is seated at the proper depth inside the tubing.

To insert the embodiment of backbone wire 820 into housing tube 120 a wire of about 32 mm in length is threaded into the lumen of the housing tube at what will become the proximal end 140 of the tube 120. The backbone wire 820 is then threaded through the distal end of the lumen of the housing tube 120 until it reaches the 32 mm wire placed at the proximal end of the tube 120. The backbone wire is marked where it exits the distal end of the tube 120. The backbone wire is then cut at the mark and is rethreaded into the lumen of the housing tube 120 so that the cut end of backbone wire 920 is flush with the distal end of housing tube 120. The distal end of the backbone wire is then welded to the distal end of tube 120 with a TIG welder. Repeated exposure to the TIG welder increases the diameter of the rounded end. This provides a rounded end 150 of the source wire that has a slightly larger diameter than tube 120 and provides an end that can be inserted into an after loader, where the source wire can be held in place by the rounded end 150 and a set screw that is tightened into the wire just below the rounded end 150.

The next step entails the placing of a plug, a stopper, or a seal in housing tube 120 where it can restrict the access of radioactive materials into the lumen of unmodified section 180. Several methods can be used.

One method of sealing the lumen of unmodified section 180 that can be used once the backbone wire 720 is determined to be properly positioned is described below. The length of backbone wire 720 on the distal end from the point where it exits the tubing to the end of the wire is measured. The backbone wire is than advanced out the proximal end and a slow drying glue or epoxy can be applied to the backbone wire a couple of centimeters distal to the rounded end 780. The backbone wire is then pulled from the distal end back into position until the length of wire exiting the distal end of the tubing matches exactly with the measured length above. At this point, the backbone wire is cut flush to the distal end 150 where it exits the tubing and is welded, soldered, epoxyed, glued, etc. permanently to the tubing. This end is then rounded.

Alternatively, this backbone wire can be attached to the inner housing at several points by means of spot welding, or the use of gluing as described above. Since backbone wire 720 has a smaller diameter than the diameter of the lumen of unmodified section 180, a small gap 730 will exist between the outer surface of the backbone wire and the inner surface of the housing tube 130 to allow the wire to be attached to the housing at different locations. These attachment sites may also serve as a seal to prevent the migration of radioactive particles and as a safety wire if the cuter housing material should break along unmodified section 180. If glue or epoxy is used, once it has dried, the cavity may be cleared of any residue glue or epoxy by reaming, drilling, honing, grinding, etc.

However, backbone wire 720 does not need to be attached to the housing tube 120 at various sites to serve as a security device. Since the larger rounded end 780 can not fit inside the lumen of the unmodified section 180 and the distal non-rounded end of the backbone wire is permanently attached to the housing at the distal end by gluing, welding, soldering, etc. if the housing tube 120 was to break along unmodified section 180, the backbone wire 720 would serve as a safety mechanism and keep the radioactive core from separating from the rest of the wire.

A similar method of sealing the lumen of the unmodified section 180 described above can be used with backbone wire 820 having a proximal end with a taper 897 and a smaller rounded end 895. This smaller rounded end 895 with the tapered segment would be positioned inside the tapered section 275 of the housing material so that a gap would exist between the inner wall 130 and the tapered rounded segment of backbone wire 830. This would allow the taper 897 to be flexible and collapsible within the housing material without any interference from the rounded end 895 of the backbone wire 820. However, this gap should not be large enough to allow the radioactive core to advance distal to the rounded backbone end 895.

Alternatively, instead of placing a backbone wire throughout the entire distal length, a small plug (or a small segment of the backbone wire) could be used by itself. The plug should be rounded as illustrated in FIG. 1 or 2. Plug 190, 290 and 590 will have to be positioned from the proximal end. A temporary backbone wire would be placed from the distal end and used as a stopper to help position the plug. A section of the plug below the rounded end 195, 295, or 595 can be permanently fixed to the housing material by means of spot welding, or by applying a slow-drying glue, epoxy, etc. to the plug prior to loading it into position. The temporary backbone wire is removed after the spot welding takes place or prior to the glue or epoxy permanently hardening into position.

Another method of securing the plug to the inner wall 130 of housing tube 120 would be to temporarily use the backbone wire as described above. Once the plug was in place, it would be held from advancing forward by a wire in the proximal end. The backbone wire would be removed and a small piece of hardening agent that would have a low melting temperature, such as solder or glue (such as the glue used for hot glue guns), would be loaded and advance from the distal end by means of the backbone wire until the hardening agent reached the plug. The tubing would be held with the proximal end down (still containing the wire positioning the plug in place) and the backbone wire would be removed. Heat (lower temperature than what would be needed to affect the properties of the plug and housing material) would be applied to the area where the hardening agent meets the plug, until the hardening agent melts and seals the plug to the inner housing wall. Once the sealing agent has dried, a quick test by trying to advance the plug in either direction would assure that the plug is fixed at the proper location.

An optional feature of the source wire embodiments is to attach the backbone wire to the inner surface of the housing tube 120 by welding, fusing, soldering, gluing, etc. Sites of attachment 830 are shown in FIG. 8. These sites of attachment 830 provide an internal safety device that insures that if the housing tube 120 were to break that the radioactive core 160 would not separate from the backbone wire 830 and could be retracted from the patient.

Attachment sites 830 may also act as seals to prevent the migration of radioactive materials into the distal regions of the unmodified section 180. Such attachment sites 830 may be made by a number of methods. One such method would be to thread the backbone wire 820 through the length of the housing tube. The distal end of the wire would be marked at the point where the proximal end of the wire is flush with the proximal end of the housing tube 120. The backbone wire would then be pushed forward and a small amount of slow drying epoxy placed around the circumference of the backbone wire 820 about two centimeters from the proximal end of the wire. Once the epoxy is added to the wire, the wire would be pulled back into the housing tube until the mark on the distal end extended from the distal end of the housing tube the appropriate distance, preferably about 32 mm. The backbone wire would then be cut flush with the distal end of the wire and welded to the housing tube to seal the distal end of the backbone wire 820. Any glue adhering to the internal surface of the proximal portion of the housing tube, where the epoxied backbone wire was drawn through the housing tube, would be reamed out before the radioactive core 160 was inserted into the backbone wire.

An alternative method of producing attachment sites 830 would be to follow the procedure described above, except to allow the epoxy to dry before drawing the proximal end of the backbone wire back into the housing tube. The epoxy ring would then be ground or sanded to fit snugly within the housing tube 120. Attachment sites 830 would encircle backbone wire 830 closing off gap 730 and thereby preventing any "flakes" from the radioactive core 160 from migrating through gap 730 between the backbone wire 820 and the inner surface of housing tube 130.

Another method to create a plug or stopper would be to use a small piece of flexible metal, latex, elastic, rubber, etc. and position distal to or at the bottom of the tapered section 275. Once again, depending on the material used, glue, epoxy, solder, welding, etc. could be used to hold the material into position.

The next step would typically be to load the radioactive core 160 into the proximal end of tubing 120. A preferred method is to set the proximal end of housing tube 120 about 0.025" above a heat sink 1010. The heat sink is also used as a clamping device to hold the wire in place. A gap of about 0.035" is set between the top of the housing tube 120 and the bottom of the welding rod. Then an iridium fiber, which has been irradiated in a nuclear reactor to the desired radioactivity and held for 11 to 14 days to purge the iridium fiber of any short lived radioactive contaminants, is removed from its container. The iridium fiber may or may not be encapsulated as described above. The iridium fiber is preferably greater than 20 mm in length and is typically about 30 mm in length and about 0.005" in outside diameter.

The radioactive iridium fiber is loaded into the housing tube 120 using a funnel. The iridium fiber is made flush with the bottom of the funnel. A small rod, having a proper length and outside diameter, is used to countersink the Ir-192 about 2 mm from the top of the housing tube 120. The funnel is then removed. The assembly of the radioactive core 160 into the housing tube 120 is done using hand manipulators behind a leaded glass with lead shields so that the human assembler is not exposed to radiation. The forceps, funnel and heat sink used during the process that may have touched the radioactive core 160 must be decontaminated or disposed of properly.

Figure 10:
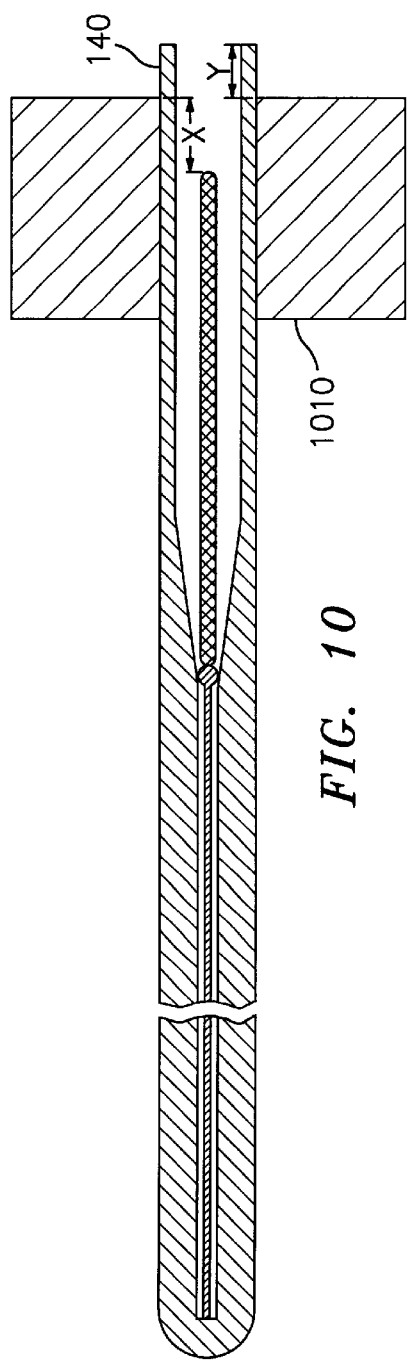
FIG. 10 shows a partial cross-section of a source wire positioned in a heat sink before its proximal end is sealed.

Once the iridium fiber, or encapsulated fiber, is set in the proximal end of the housing tube 120, as illustrated in FIG. 10, the exposed proximal end 140 of tube 120 is subjected to the heat of a TIG welder. This fuses the exposed end of the housing tube. Without the heat sink the heat would go directly to the iridium fiber and would oxidize, vaporize or fracture the iridium core 160 causing contamination of the outside surface of the source wire rendering it unusable. However, if the housing tube is placed a distance Y above the heat sink 1010 and the radioactive core 160 is placed a distance X below the top of the heat sink 1010 then the TIG welder will cause the tube 120 to seal the proximal end 140 of the source wire without affecting the radioactive core 160. As long as the distances between the top of the housing tube and the heatsink, as well as the top of the housing tube and the bottom of the welding rod are correct, a rounded surface ranging from about 0.016" to about 0.018" in diameter results. The size of the rounded area is verified with gauges so that the resulting source wire will fit into the internal diameter of the positioning catheter that is used to properly place the radioactive source wire at the treatment site. Once the source wire has been fabricated, it is wiped clean with swabs and loaded into a lead container to await use in a patient.

Having described several embodiments of the new and improved flexible source wire for radiation treatment in accordance with the present invention, it is believed that other modifications, variations and changes will be suggested to those skilled in the art in view of the description set forth above. It is therefor to be understood that all such variations, modifications and changes are believed to fall within the scope of the invention as defined in the appended claims.

What is claimed is:

1. A process for manufacturing a radioactive source wire for irradiating diseased tissue, said process comprising the steps of:
   providing a thin, flexible tube, said tube having a wall thickness, an interior surface, an exterior surface, a distal end, a proximal end, and a lumen;
   enlarging the lumen of said proximal end of said tube to form a modified segment, wherein a wall thickness of said modified segment is thinner than a wall thickness of an unmodified section adjoining the modified segment;
   inserting a plug into said tube, wherein a portion of said plug is located in the lumen of said unmodified section;
   inserting a radioactive core into the modified segment of said tube; and
   sealing said distal end and said proximal end of said tube;
   said tube, plug, and radioactive core forming a composite source wire for performing radiation treatment.

2. The process of claim 1, wherein said tube is made of a nickel/titanium alloy.

3. The process of claim 1, further comprising a step of tapering a portion of said interior surface of said tube, said tapered portion localized between said unmodified section and said modified segment.

4. The process of claim 1, wherein said step of inserting a plug includes a step of attaching said plug to an interior surface of said unmodified section.

5. The process of claim 1, further comprising a step of inserting a capsule into said modified segment of said tube, said capsule capable of accepting said radioactive core.

6. The process of claim 1, further comprising the step of encapsulating the radioactive core prior to inserting said radioactive core into the modified segment.

7. The process of claim 1, wherein said radioactive core has a rounded end.

8. The process of claim 7, wherein said step of inserting said radioactive core includes inserting said rounded end to abut said plug.

9. The process of claim 1, further comprising the step of coating said exterior surface of said tube with a non-oxidizing agent.

10. The process of claim 9, wherein said non-oxidizing agent is gold.

11. The process of claim 1, wherein the step of sealing said proximal end further comprises applying a heat sink to said exterior surface of said tube, said heat sink a distance Y from the proximal end of said tube, and applying sufficient heat to said proximal end of said tube to melt said proximal end extending beyond said heat sink.

12. A process for manufacturing a radioactive source wire for irradiating diseased tissue, said process comprising:
   providing a thin, flexible tube having a wall thickness, an interior surface, an outer surface, a distal end, a proximal end, and a lumen;
   enlarging the lumen of said proximal end of said tube to form a modified segment, wherein a wall thickness of said modified segment is thinner than a wall thickness of an unmodified section adjoining said modified segment;
   tapering a portion of said interior surface of said tube, said tapered portion localized between said unmodified section and said modified segment;
   inserting a backbone wire into the lumen of said distal end of said tube for a predetermined distance;
   applying a heat sink to the outer surface of said tube, said heat sink having a proximal end situated a distance Y from the proximal end of said tube;
   inserting a radioactive core into the lumen of the proximal end of said tube a distance X+Y from the proximal end of said tube; and
   applying sufficient heat to said proximal end of said tube to melt said proximal end extending beyond said heat sink.

13. A process for manufacturing a radioactive source wire for irradiating diseased tissue, said process comprising:
   providing a thin, flexible tube having a wall thickness, an interior surface, an outer surface, a distal end, a proximal end, and a lumen;
   enlarging the lumen of said proximal end of said tube to form a modified segment, wherein a wall thickness of said modified segment is thinner than a wall thickness of an unmodified section adjoining said modified segment;
   tapering a portion of said interior surface of said tube, said tapered portion localized between said unmodified section and said modified segment;
   inserting a plug into said tube, wherein a portion of said plug is located in the lumen of said unmodified section;
   applying a heat sink to the outer surface of said tube, said heat sink having a proximal end situated a distance Y from the proximal end of said tube;
   inserting a radioactive core into the lumen of the proximal end of said tube a distance X+Y from the proximal end of said tube; and
   applying sufficient heat to said proximal end of said tube to melt said proximal end extending beyond said heat sink.

14. A process for manufacturing a radioactive source wire for irradiating diseased tissue, said process comprising:
   providing a thin, flexible tube having a wall thickness, an interior surface, an outer surface, a distal end, a proximal end, and a lumen;
   enlarging the lumen of said proximal end of said tube to form a modified segment, wherein a wall thickness of said modified segment is thinner than a wall thickness of an unmodified section adjoining said modified segment;
   tapering a portion of said interior surface of said tube, said tapered portion localized between said unmodified section and said modified segment;
   providing a flexible backbone wire having a first end, a second end and a circumference;

inserting said first end of said backbone wire into the lumen of said distal end of said tube;

threading said backbone wire through said lumen until said fist end extends beyond said proximal end of said tube;

applying an epoxy around the circumference of said backbone wire extending from said proximal end of said tube;

removing excess epoxy along said predetermined distance of said lumen and said tube;

inserting a radioactive core into the lumen of said proximal end of said tube; and sealing said distal end and said proximal end of said tube.

15. A process for manufacturing a housing tube for a source wire for irradiating diseased tissue, said process comprising:

providing a thin, flexible tube having a wall thickness, an interior surface, an outer surface, a distal end, a proximal end, and a lumen;

enlarging the lumen of said proximal end of said tube to form a modified segment, wherein a wall thickness of said modified segment is thinner than a wall thickness of a unmodified section adjoining said modified segment; and reinforcing a weak point in the wall of said tube.

16. The process of claim 15, further comprising tapering a portion of an interior surface of said tube, said tapered portion localized between said unmodified section and said modified segment.

17. The process of claim 15, wherein reinforcing a weak point in the wall of said tube includes sealing breaks in the integrity of the tube.

18. The process of claim 17, wherein sealing breaks in the integrity of the tube is accomplished by honing, glazing, heating, filling with flexible hardeners, filling with bonding agents, or a combination thereof.

* * * * *